United States Patent
Kim et al.

(10) Patent No.: US 11,472,754 B2
(45) Date of Patent: *Oct. 18, 2022

(54) OLIGOMER PREPARATION METHOD AND OLIGOMER PREPARATION APPARATUS

(71) Applicant: LG CHEM, LTD., Seoul (KR)

(72) Inventors: Mi Kyung Kim, Daejeon (KR); Eun Kyo Kim, Daejeon (KR); Hye Bin Kim, Daejeon (KR); Joon Ho Shin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/422,398

(22) PCT Filed: Aug. 12, 2020

(86) PCT No.: PCT/KR2020/010679
§ 371 (c)(1),
(2) Date: Jul. 12, 2021

(87) PCT Pub. No.: WO2021/033993
PCT Pub. Date: Feb. 25, 2021

(65) Prior Publication Data
US 2022/0089509 A1    Mar. 24, 2022

(30) Foreign Application Priority Data
Aug. 21, 2019    (KR) ........................ 10-2019-0102509

(51) Int. Cl.
C07C 2/06    (2006.01)
C07C 7/00    (2006.01)
C07C 7/04    (2006.01)

(52) U.S. Cl.
CPC ................ *C07C 2/06* (2013.01); *C07C 7/005* (2013.01); *C07C 7/04* (2013.01)

(58) Field of Classification Search
CPC ........... C07C 2/06; C07C 7/005; B01D 3/143; B01J 19/24; B01J 2219/00042
See application file for complete search history.

(56) References Cited

U.S. PATENT DOCUMENTS 6,045,661 A    4/2000    Kreischer et al.
2007/0185362 A1    8/2007    Lattner et al.
(Continued)

FOREIGN PATENT DOCUMENTS

JP    2009120588 A    6/2009
JP    2016-531165 A    10/2016
(Continued)

*Primary Examiner* — Ali Z Fadhel
(74) *Attorney, Agent, or Firm* — Dentons US LLP

(57) ABSTRACT

Provided are a method for preparing an oligomer and an apparatus for preparing an oligomer. The method for preparing an oligomer includes performing an oligomerization reaction by feeding a feed stream containing a monomer to a reactor; feeding a first discharge stream of the reactor to a first separation device, and feeding a second discharge stream of the reactor to a second separation device; feeding a lower discharge stream of the second separation device to a third separation device; feeding an upper discharge stream containing the monomer of the third separation device to a monomer dissolution device and dissolving the upper discharge stream in a solvent fed to the monomer dissolution device; and feeding a discharge stream of the monomer dissolution device to the reactor.

12 Claims, 1 Drawing Sheet

(56) References Cited

U.S. PATENT DOCUMENTS

| | | | |
|---|---|---|---|
| 2013/0102826 A1* | 4/2013 | Lattner | C07C 2/08 585/510 |
| 2013/0296483 A1 | 11/2013 | Yokota et al. | |
| 2016/0368834 A1 | 12/2016 | Nyce et al. | |
| 2018/0355075 A1 | 12/2018 | Ali et al. | |

FOREIGN PATENT DOCUMENTS

| | | |
|---|---|---|
| KR | 10-2012-0123131 A | 11/2012 |
| KR | 10-2015-0043313 A | 4/2015 |
| KR | 10-2016-0119812 A | 10/2016 |
| KR | 10-2017-0028203 A | 3/2017 |
| KR | 10-2018-0082573 A | 7/2018 |
| KR | 10-2019-0063840 A | 6/2019 |
| WO | 2012-39838 A2 | 3/2012 |

\* cited by examiner

OLIGOMER PREPARATION METHOD AND OLIGOMER PREPARATION APPARATUS

CROSS-REFERENCE TO RELATED APPLICATIONS

This application is a National Phase entry pursuant to U.S.C. § 371 of International Application No. PCT/KR2020/010679, filed on Aug. 12, 2020, and claims the benefit of and priority to Korean Patent Application No. 10-2019-0102509, filed on Aug. 21, 2019, the entire contents of which are incorporated by reference in their entirety for all purposes as if fully set forth herein.

TECHNICAL FIELD

The present invention relates to a method for preparing an oligomer and an apparatus for preparing an oligomer, and more particularly, to a method for preparing an oligomer and an apparatus for preparing an oligomer capable of efficiently recycling a monomer recovered in a process for producing an oligomer.

BACKGROUND ART

Alpha-olefin, which is an important substance used for a comonomer, a detergent, a lubricant, a plasticizer, etc., has been commercially widely used, and among them, 1-hexene and 1-octene have been mainly used as a comonomer for controlling a density of polyethylene when producing linear low density polyethylene (LLDPE).

The alpha-olefin such as 1-hexene and 1-octene has been typically produced through an ethylene oligomerization reaction. The ethylene oligomerization reaction is performed by an oligomerization reaction (trimerization reaction or tetramerization reaction) of ethylene using ethylene as a reactant, and a product produced by the above reaction contains unreacted ethylene as well as a multi-component hydrocarbon mixture containing the desired 1-hexene and 1-octene. The product is subjected to a separation process through a distillation column. In this case, the unreacted ethylene is recovered and reused for the ethylene oligomerization reaction.

In recovering the unreacted ethylene, a separation device such as a distillation column or a flash drum is used in order to reduce an amount of product or by-product such as solvent in an unreacted ethylene stream to be recovered. In this case, a difference in a boiling point between the unreacted ethylene and the product is large, and thus, a difference between temperatures of upper and lower portions of the separation device also becomes also large. The temperatures of the upper and lower portions of the separation device are determined depending on a pressure of the separation device. When the pressure of the separation device is high, the temperatures of upper and lower portions are increased, and when the pressure of the separation device is low, the temperatures of upper and lower portions are lowered. When the pressure of the separation device is increased, the temperature of the upper portion of the separation device is increased, such that the unreacted ethylene is easily recovered, but the temperature of the lower portion of the separation device is also increased, and a decomposition and a reaction of hydrocarbons such as a product and a solvent may thus be promoted, resulting in a low yield of the product. On the other hand, when the pressure of the separation device is decreased, a side reaction of the hydrocarbons may be suppressed, but the temperature of the upper portion of the separation device is decreased, and a low-temperature refrigerant is thus required when recovering the unreacted ethylene. In this case, a process cost is increased.

In addition, the unreacted ethylene may be recovered in a gas-phase or a liquid-phase. In order to recover the unreacted ethylene and reuse the recovered unreacted ethylene for the ethylene oligomerization reaction, a pressure of the recovered unreacted ethylene stream should be increased up to a pressure of a reactor. Conventionally, in order to increase the pressure of the unreacted ethylene stream to the pressure of the reactor using a pump, the unreacted ethylene stream should be a liquid-phase. To this end, the unreacted ethylene stream should be cooled to −25° C. or less using a very low-temperature refrigerant due to a low boiling point of ethylene. In addition, there is a problem that the pressure of the recovered unreacted ethylene stream should be increased up to the pressure of the reactor by separately installing a compressor, in order to recover the unreacted ethylene in the gas-phase.

As such, a conventional method for recovering the unreacted ethylene and reusing the recovered unreacted ethylene for an oligomerization reaction has problems that a production yield of the product is low, an investment cost is high and economical efficiency is low, for example, a very low temperature refrigerant is used, or the compressor is separately installed.

DISCLOSURE

Technical Problem

An object of the present invention is to provide a method for preparing an oligomer and an apparatus for preparing an oligomer with a reduced investment cost.

That is, an object of the present invention is to provide a method for preparing an oligomer and an apparatus for preparing an oligomer capable of reducing an investment cost, improving economical efficiency, and preventing a reduction in a production yield of a product because there is no need to use a very low-temperature refrigerant or install a separate compressor, in recovering unreacted ethylene and reusing the recovered unreacted ethylene for an oligomerization reaction in a process for producing an oligomer.

Technical Solution

According to an exemplary embodiment of the present invention, a method for preparing an oligomer includes: performing an oligomerization reaction by feeding a feed stream containing a monomer to a reactor; feeding a first discharge stream of the reactor to a first separation device and feeding a second discharge stream of the reactor to a second separation device; feeding a lower discharge stream of the second separation device to a third separation device; feeding an upper discharge stream containing a monomer of the third separation device to a monomer dissolution device and dissolving the upper discharge stream in a solvent fed to the monomer dissolution device; and feeding a discharge stream of the monomer dissolution device to the reactor.

According to another exemplary embodiment of the present invention, an apparatus for preparing an oligomer includes: a reactor oligomerizing a feed stream containing a fed monomer, feeding a first discharge stream to a first separation device, and feeding a second discharge stream to a second separation device; a first separation device receiving the first discharge stream of the reactor; a second separation device receiving the second discharge stream of the reactor and feeding a lower discharge stream to a third separation device; a third separation device receiving a lower discharge stream of the second separation device and feeding an upper discharge stream containing a monomer to a monomer dissolution device; and a monomer dissolution device dissolving the fed upper discharge steam of the third separation device in a separately fed solvent and feeding a discharge stream to the reactor.

Advantageous Effects

According to the method for preparing an oligomer and the apparatus for preparing an oligomer according to the present invention, it is possible to suppress a side reaction of hydrocarbons by lowering a temperature of a lower portion of the second separation device while maintaining an upper portion of the second separation device at a high temperature even though the second separation device is operated at a high pressure, by discharging some unreacted monomers as a lower discharge stream of the second separation device to the third separation device while operating the second separation device at the high pressure in recovering unreacted monomers.

Further, a low-pressure unreacted monomer recovered from the third separation device is dissolved in a solvent and fed to the reactor, such that a low-temperature refrigerant and installation of an additional compressor required in a conventional process for recovering the unreacted monomer are not required.

In addition, when the recovered unreacted monomer is dissolved in the solvent, the unreacted monomer can be dissolved at a relatively high temperature, a dissolution rate of the unreacted monomer is excellent, and a pressure of the solvent stream in which the unreacted monomer is dissolved is increased due to a feeding pressure of the solvent fed to the monomer dissolution device, and the pressure of the solvent stream can thus be increased up to the pressure of the reactor using only a pump.

DETAILED DESCRIPTION

Figure 1:
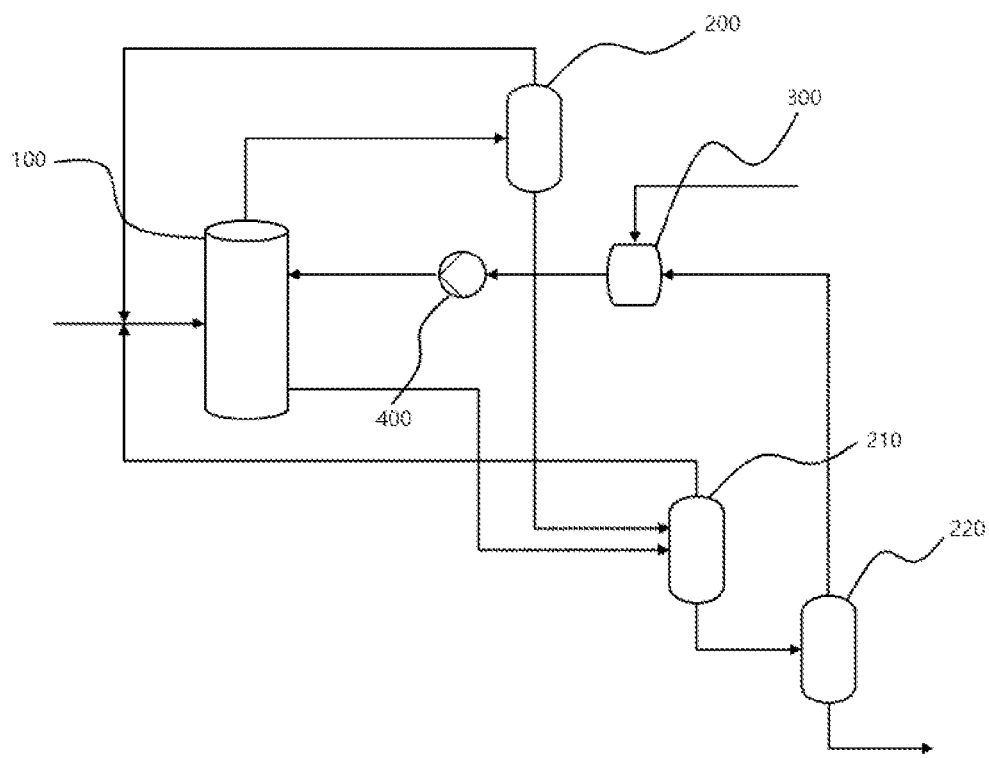
FIG. 1 is a process flowchart of a method for preparing an oligomer according to an exemplary embodiment of the present invention.

The terms and words used in the detailed description and claims should not be interpreted as being limited to conventional or dictionary meanings, but should be interpreted as having meanings and concepts meeting the technical ideas of the present invention based on a principle that the inventors can appropriately define the concepts of terms in order to describe their own inventions in the best mode.

The term 'stream' used herein may refer to a flow of fluid in a process, and may also refer to a fluid itself flowing in a pipe. Specifically, the 'stream' may refer to both of a fluid itself flowing in a pipe connecting respective devices to each other and a flow of the fluid. In addition, the fluid may refer to a gas or a liquid.

Hereinafter, the present invention will be described in more detail to assist in understanding the technical idea of the present invention.

According to the present invention, there is provided a method for preparing an oligomer. As the method for preparing an oligomer, there is provided a method for preparing an oligomer including: performing an oligomerization reaction by feeding a feed stream containing a monomer to a reactor; feeding a first discharge stream of the reactor to a first separation device and feeding a second discharge stream of the reactor to a second separation device; feeding a lower discharge stream of the second separation device to a third separation device; feeding an upper discharge stream containing a monomer of the third separation device to a monomer dissolution device and dissolving the upper discharge stream in a solvent fed to the monomer dissolution device; and feeding a discharge stream of the monomer dissolution device to the reactor.

According to an exemplary embodiment of the present invention, in the performing of the oligomerization reaction by the feeding of the feed stream containing the monomer to the reactor, the feed stream containing the monomer can be fed to the reactor, and an oligomerization reaction of the monomer can be performed in a liquid-phase at a lower portion of the reactor. The oligomerization reaction may refer to a reaction in which the monomer is oligomerized. Depending on the number of monomers to be polymerized, the oligomerization reaction is called trimerization and tetramerization, which are collectively called multimerization.

According to an exemplary embodiment of the present invention, the monomer can be ethylene, and the oligomer can be alpha-olefin. The alpha-olefin, which is an important substance used for a comonomer, a detergent, a lubricant, a plasticizer, etc., is commercially widely used, and among them, 1-hexene and 1-octene are mainly used as a comonomer for controlling a density of polyethylene when producing linear low density polyethylene (LLDPE). The alpha-olefin such as 1-hexene and 1-octene can be produced, for example, through a trimerization reaction or a tetramerization reaction of the ethylene.

According to an exemplary embodiment of the present invention, the oligomerization reaction of the monomer can be performed in a reactor suitable for a continuous process, and can be performed preferably under a reaction system including at least one reactor selected from the group consisting of a continuous stirred tank reactor (CSTR) and a plug flow reactor (PFR).

According to an exemplary embodiment of the present invention, the oligomerization reaction of the monomer can be performed as a homogeneous liquid-phase reaction, a slurry reaction in which the catalyst system is partially insoluble or entirely insoluble, a two-phase liquid/liquid reaction, or a bulk-phase or gas-phase reaction in which a product acts as a main medium, under the presence or absence of a solvent by applying the reaction system and a general contact technique. Preferably, the oligomerization reaction of the monomer can be performed as a homogeneous liquid-phase reaction.

According to an exemplary embodiment of the present invention, the oligomerization reaction can be performed at a temperature of 5° C. to 200° C., 10° C. to 180° C., or 30° C. to 150° C. In addition, the oligomerization reaction can be performed under a pressure of 1 bar to 100 bar, 10 bar to 80 bar, or 20 bar to 60 bar. When the ethylene is oligomerized within the above temperature and pressure ranges, selectivity for the desired alpha-olefin can be excellent, an amount of by-product can be reduced, operational efficiency of the continuous process can be increased, and a cost can be reduced.

According to an exemplary embodiment of the present invention, the feed stream containing the monomer can contain a gas-phase monomer, a liquid-phase monomer, and a solvent.

The gas-phase monomer contained in the feed stream can be fed as a feed stream containing directly an ethylene monomer separated in, for example, a naphtha cracking center (NCC) process or containing a monomer after being subjected to a storing step. In addition, the gas-phase monomer can include a stream recovered in a process for producing an oligomer.

The liquid-phase monomer fed to the reactor as the feed stream can include a stream recovered in the process for producing an oligomer. In addition, the liquid-phase monomer can include a stream obtained by dissolving a gas-phase monomer recovered in the process for producing an oligomer in the solvent.

The solvent contained in the feed stream may refer to a solvent for dissolving the recovered gas-phase monomer. In some cases, the solvent can be additionally fed to the reactor as a separate feed stream in addition to the solvent for dissolving the monomer.

According to an exemplary embodiment of the present invention, in the feeding of the first discharge stream of the reactor to the first separation device and the feeding of the second discharge stream of the reactor to the second separation device, the separation device can use a general distillation column.

According to an exemplary embodiment of the present invention, the first discharge stream can be a stream containing a gas-phase monomer. The first separation device can feed the upper discharge stream containing the gas-phase monomer to the reactor and feed the lower discharge stream containing the liquid-phase monomer to the second separation device. Here, the upper discharge stream of the first separation device can be mixed with a gas-phase monomer stream separately fed to the reactor in a mixer and be fed to the reactor or be separately fed to the reactor.

According to an exemplary embodiment of the present invention, the second discharge stream of the reactor can be a stream containing the liquid-phase monomer. The second discharge stream of the reactor can be separated into the upper discharge stream fed to the second separation device and containing a gas-phase monomer and the lower discharge stream containing the liquid-phase monomer.

The gas-phase monomer recovered as the upper discharge stream in the second separation device can be fed to the reactor. In this case, the upper discharge stream of the second separation device can be mixed with the gas-phase monomer stream separately fed to the reactor and the upper discharge stream of the first separation device in the mixer and be fed to the reactor or be separately fed to the reactor.

The lower discharge stream of the second separation device containing the liquid-phase monomer can further contain an oligomer and a solvent. The lower discharge stream of the second separation device containing the liquid-phase monomer, the oligomer, and the solvent can be fed to the third separation device and can be separated into the upper discharge stream containing a gas-phase monomer and the lower discharge stream containing the liquid-phase solvent and the oligomer in the third separation device.

The second separation device can be operated at a pressure higher than that in the third separation device. Specifically, the second separation device discharges the lower discharge stream containing the monomer to the third separation device while being operated at a high pressure, such that it is possible to lower the temperature of the lower portion of the second separation device while maintaining the upper portion of the second separation device at a high temperature. Therefore, the side reaction of the hydrocarbons can be suppressed. In detail, it is possible to easily recover the unreacted monomer in the upper portion of the second separation device and prevent the produced oligomer from being decomposed or a side reaction that the produced oligomer reacts with other substances to generate by-products from occurring in the lower portion of the second separation device by maintaining the upper portion of the second separation device at the high temperature and reducing the temperature of the lower portion of the second separation device while operating the second separation device at the high pressure.

The pressure in the second separation device can be in a range of 10 bar to 50 bar, and the pressure in the third separation device can be in a range of 0.5 bar to 15 bar. For example, the pressure in the second separation device can be in a range of 10 bar to 50 bar, 15 bar to 40 bar, or 20 bar to 30 bar, and the pressure in the third separation device can be in a range of 0.5 bar to 15 bar, 1 bar to 10 bar or 2 bar to 5 bar. The pressures in the second and third separation devices are controlled to be in the above ranges, such that it is possible to efficiently recover the unreacted monomer without using a low-temperature refrigerant or installing an additional compressor in the second and third separation devices and it is possible to prevent the oligomer produced through the oligomerization reaction of the monomer from being decomposed or the side reaction that the oligomer reacts with other substances to generate the by-products from occurring in the lower portion of the second separation device.

The gas-phase monomer can be recovered as the upper discharge stream in the third separation device, and the upper discharge stream of the third separation device can pass through the monomer dissolution device and be then fed to the reactor. In addition, in the lower stream of the third separation device, the solvent and the oligomer can be separated through an additional separation process, and the separated solvent can be fed to the reactor. In addition, the separated oligomer can again be separated into a trimer, a tetramer, etc., of a monomer through an additional separation process.

A pressure of the upper discharge stream of the third separation device can be 0.5 bar to 15 bar. For example, the pressure of the upper discharge stream of the third separation device can be in a range of 0.5 bar to 15 bar, 1 bar to 10 bar, or 2 bar to 5 bar. As described above, the third separation device is operated at a pressure of 0.5 bar to 15 bar, which is lower than that of the second separation device. Thus, the pressure of the upper discharge stream of the third separation device is also in a range of 0.5 bar to 15 bar and the upper discharge stream is discharged as a low-pressure gas-phase stream. As described above, when the pressure of the gas-phase upper discharge stream of the third separation device is 0.5 bar to 15 bar, the pressure of the upper discharge stream should be increased up to the pressure of the reactor in order to feed the upper discharge stream to the reactor. In order to increase the pressure of the low-pressure gas-phase stream, a separate compressor should be installed in the related art. However, in the method for preparing an oligomer according to the present invention, the upper discharge stream of the third separation device having the pressure of 0.5 bar to 15 bar is fed to the monomer dissolution device, dissolved in the solvent, and then fed in the liquid-phase to the reactor, such that it is possible to solve a problem such as an increase in a process cost caused by separate installation of the compressor.

According to an exemplary embodiment of the present invention, the monomer contained in the upper discharge stream of the third separation device can be dissolved in the solvent separately fed to the monomer dissolution device in the monomer dissolution device. Specifically, the upper discharge stream containing a gas-phase monomer of the third separation device can be fed to the monomer dissolution device and mixed with the solvent fed to the monomer dissolution device to dissolve the gas-phase monomer in the solvent.

The solvent fed to the monomer dissolution device can be at least one selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene. As a specific example, the solvent can be a mixture of two solvents. As a more specific example, the solvent can be a mixture of methylcyclohexane and decane. When a mixture of the two solvents is used as the solvent, in the dissolving of the monomer in the solvent, the monomer can be liquefied at a higher temperature, and the dissolution rate of the monomer can be improved.

A temperature of the solvent fed to the monomer dissolution device can be in a range of 1° C. to 50° C., and a pressure of the solvent can be in a range of 10 bar to 100 bar. For example, a feed temperature of the solvent can be in a range of 1° C. to 50° C., 10° C. to 40° C., or 25° C. to 35° C., and a feed pressure of the solvent can be in a range of 10 bar to 100 bar, 15 bar to 70 bar, or 20 bar to 50 bar. The solvent is fed to the monomer dissolution device in the above temperature and pressure ranges, such that the monomer can be liquefied at a relatively high temperature in the monomer dissolution device, and a pressure of the discharge stream of the monomer dissolution device can be increased up to the pressure of the reactor using only a pump.

A content of the solvent fed to the monomer dissolution device can be in a range of 0.5 times to 10 times, 0.8 times to 5 times, or 1 time to 1.1 times the content of oligomer product in the second discharge stream discharged from the reactor. The solvent having the content in the above range is fed, such that the oligomer product can be efficiently produced with a similar amount of solvent to an amount of the solvent used in the conventional method for preparing an oligomer.

According to an exemplary embodiment of the present invention, the method for preparing an oligomer can include feeding a discharge stream of the monomer dissolution device to the reactor, and the discharge stream of the monomer dissolution device can be a liquid-phase stream containing a monomer dissolved in the solvent. Specifically, the upper discharge stream of the third separation device contains a gas-phase monomer, and in the related art, in order to feed the gas-phase monomer directly to the reactor, a separate compressor for increasing a pressure of the gas-phase monomer up to the pressure of the reactor is required. Alternatively, there is a method for cooling the gas-phase monomer to a liquid-phase and increasing a pressure of the gas-phase monomer up to the pressure of the reactor through a pump. In this case, a very low-temperature refrigerant is required in order to cool the gas-phase monomer to the liquid-phase. However, the method for preparing an oligomer according to the present invention solves the conventional problem by dissolving the gas-phase monomer in the solvent and then feeding the dissolved gas-phase monomer in the liquid-phase to the reactor.

A temperature of the discharge stream of the monomer dissolution device can be in a range of −5° C. to 50° C. For example, the temperature of the discharge stream of the monomer dissolution device can be in a range of −5° C. to 50° C., 0° C. to 40° C., or 5° C. to 30° C. In the conventional method for preparing an oligomer, in order to cool the recovered gas-phase monomer to the liquid-phase, the recovered gas-phase monomer should be cooled to a temperature of about −25° C. or less using the very low-temperature refrigerant. Thus, there is a problem such as an increase in a cost due to the use of an expensive refrigerant and energy loss for heating when the low-temperature liquid-phase monomer is fed to the reactor. However, the method for preparing an oligomer according to the present invention solves the problem described above by dissolving the recovered gas-phase monomer in the solvent, and then feeding the dissolved gas-phase monomer to the reactor.

According to an exemplary embodiment of the present invention, a pressure of the discharge stream of the monomer dissolution device can be in a range of 1 bar to 100 bar. For example, the pressure of the discharge stream of the monomer dissolution device can be in a range of 10 bar to 80 bar, 15 bar to 70 bar, or 25 bar to 60 bar. The pressure of the discharge stream of the monomer dissolution device can be implemented only by the feed pressure of the solvent fed to the monomer dissolution device. As such, the pressure of the discharge stream of the monomer dissolution device is high, and can thus be increased up to the pressure of the reactor using only the pump. Therefore, an additional device or process is not required, such that a process can be simplified and a process cost can be reduced.

According to an exemplary embodiment of the present invention, the method for preparing an oligomer can satisfy the following General Equation 1:

$$M2/M1 * 100 \geq 90\% \qquad \text{[General Equation 1]}$$

wherein M1 is a monomer content in the upper discharge stream of the third separation device, and M2 is a monomer content in the discharge stream of the monomer dissolution device. Specifically, General Equation 1 can mean a dissolution rate of the monomer dissolved in the solvent in the discharge stream of the monomer dissolution device, when the monomer recovered as the upper discharge stream in the second separation device is dissolved in the solvent in the monomer dissolution device and is discharged as the discharge stream of the monomer dissolution device. Here, the dissolution rate of the monomer dissolved in the solvent can be 90% to 100%, 95% to 100%, or 98% to 100%. As such, 90% or more or the entire amount of the recovered monomer is dissolved in the solvent and is recovered to the reactor, such that a reuse rate of the monomer is excellent. Thus, oligomer production efficiency can be improved and a process cost can be reduced.

According to the present invention, there is provided an apparatus for preparing an oligomer. As the apparatus for preparing an oligomer, there is provided an apparatus for preparing an oligomer including: a reactor oligomerizing a feed stream containing a fed monomer, feeding a first discharge stream to a first separation device, and feeding a second discharge stream to a second separation device; a first separation device receiving the first discharge stream of the reactor; a second separation device receiving the second discharge stream of the reactor and feeding a lower discharge stream to a third separation device; a third separation device receiving a lower discharge stream of the second separation device and feeding an upper discharge stream containing a monomer to a monomer dissolution device; and a monomer dissolution device dissolving the fed upper discharge stream of the third separation device in a separately fed solvent and feeding the discharge stream to the reactor.

According to an exemplary embodiment of the present invention, the apparatus for preparing an oligomer according to the present invention can be a device for performing a process of the method for preparing an oligomer described above.

According to an exemplary embodiment of the present invention, the apparatus for preparing an oligomer according to the present invention can be described with reference to FIG. 1. For example, the apparatus for preparing an oligomer can include a reactor 100 oligomerizing a feed stream containing a fed monomer, and a first discharge stream containing a gas-phase monomer can be fed from the reactor 100 to a first separation device 200 and a second discharge stream containing a liquid-phase monomer can be fed from the reactor 100 to a second separation device 210.

According to an exemplary embodiment of the present invention, the feed stream fed to the reactor 100 can contain a monomer and a solvent. Specifically, the feed stream can contain a gas-phase monomer, a liquid-phase monomer, and a solvent. The feed stream containing the gas-phase monomer can contain a gas-phase monomer stream fed directly to the reactor 100, a gas-phase monomer recovered as an upper discharge stream in the first separation device 200, and a gas-phase monomer recovered as an upper discharge stream in the second separation device 210. The gas-phase monomer stream directly fed to the reactor 100, the upper discharge stream of the first separation device 200 containing the gas-phase monomer, and the upper discharged stream of the second separation device 210 containing the gas-phase monomer can be fed individually to the reactor 100 or can be fed as a mixed discharge stream mixed in a mixer (not illustrated) to the reactor 100.

In addition, the stream containing the liquid-phase monomer in the feed stream fed to the reactor 100 can include a discharged stream of a monomer dissolution device 300 obtained by dissolving an upper discharged stream containing a gas-phase monomer separated in a third separation device 220 in the solvent. Here, the upper discharge stream of the third separation device 220 can be dissolved in a solvent separately fed to the monomer dissolution device 300 in the monomer dissolution device 300, and then be fed to the reactor 100 through a pump 400.

According to an exemplary embodiment of the present invention, the first separation device 200 can receive the first discharge stream from the reactor 100 and separate the first discharge stream into an upper discharge stream containing a gas-phase monomer and a lower discharge stream containing a liquid-phase monomer. In this case, the upper discharge stream of the first separation device 200 can be fed to the reactor 100, and the lower discharge stream of the first separation device 200 can be fed to the second separation device 210.

According to an exemplary embodiment of the present invention, the second separation device 210 can receive the second discharge stream of the reactor 100 containing the liquid-phase monomer and the lower discharge stream of the first separation device 200 and separate the second discharge stream and the lower discharge stream into an upper discharge stream containing a gas-phase monomer and a lower discharge stream containing a liquid-phase monomer. In this case, the upper discharge stream of the second separation device 210 can be fed to the reactor 100, and the lower discharge stream of the second separation device 210 can be fed to the third separation device 220.

According to an exemplary embodiment of the present invention, the third separation device 220 can receive the lower discharge stream containing the liquid-phase monomer from the second separation device 210 and separate the lower discharge stream into an upper discharge stream containing a gas-phase monomer and a lower discharge stream containing a solvent and an oligomer product. In this case, the upper discharge stream of the third separation device 220 can be fed to the monomer dissolution device 300. In addition, the oligomer product and the solvent contained in the lower discharge stream of the third separation device 220 can be separated through an additional separation device (not illustrated), and the separated solvent can be reused in a process for producing an oligomer. In addition, when an oligomerization reaction is performed using an ethylene monomer as the monomer, the oligomer product can include 1-hexene and 1-octene. In this case, the 1-hexene and the 1-octene can be separated through an additional separation device (not illustrated) or can be separated and used through a separate process.

According to an exemplary embodiment of the present invention, the monomer dissolution device 300 can receive the upper discharge stream of the third separation device 220 and dissolve the upper discharge stream in a solvent separately fed to the monomer dissolution device 300.

According to an exemplary embodiment of the present invention, the pump 400 can feed a discharge stream of the monomer dissolution device 300 containing a liquid-phase monomer formed by dissolving the gas-phase monomer in the solvent to the reactor 100. In addition, in this process, a pressure of the discharge stream of the monomer dissolution device 300 can be increased to a pressure of the reactor 100.

The method and the apparatus for preparing an oligomer according to the present invention have been described and have been shown in the drawings hereinabove, but only essential configurations for understanding the present invention have been described and have illustrated in the drawings, and processes and devices that are not separately described and illustrated, in addition to processes and devices described above and illustrated in the drawings, can be appropriately applied and used in order to implement the method and the apparatus for preparing an oligomer according to the present invention.

Hereinafter, the present invention will be described in detail with reference to the following Examples. However, the following Examples describe the present invention by way of example only. It is apparent to those skilled in the art that various changes and modifications can be made within the scope and spirit of the present invention and that the present invention is not limited thereto.

EXAMPLE

For the process flowchart illustrated in FIG. 1, a process was simulated using an Aspen Plus simulator commercially available from Aspen Technology, Inc. In this case, ethylene (C2) was fed as a monomer to the reactor 100 at 1,000 kg/hr, reaction conditions of the reactor 100 were set so that a temperature was 70° C. and a pressure was 30 bar, methylcyclohexane was used as the solvent, and an amount of fed solvent was 1 time the sum of a product and a by-product in a second discharge stream fed from the reactor 100 to the second separation device 210. The results are shown in Table 1 below.

TABLE 1

|  | Stream 1 | Stream 2 | Stream 3 | Stream 4 | Stream 5 | Stream 6 | Stream 7 | Stream 8 |
|---|---|---|---|---|---|---|---|---|
| Phase | Liquid-phase | Gas-phase | Liquid-phase | Gas-phase | Liquid-phase | Liquid-phase | Liquid-phase | Liquid-phase |
| Temperature (° C.) | 70 | 40 | 160 | 54 | 161 | 35 | 41 | 45 |
| Pressure (bar) | 30 | 15 | 15 | 6 | 6 | 30 | 6 | 30 |
| Total flow rate (Kg/hr) | 2742.4 | 550.1 | 2192.3 | 193.3 | 1990.1 | 990.8 | 1184.1 | 1184.1 |
| Lights (kg/hr) | 210.2 | 48.8 | 161.4 | 154.2 | 0.1 | 0.0 | 154.2 | 154.2 |
| Ethylene (Kg/hr) | 493.2 | 469.6 | 23.6 | 22.6 | 0.0 | 0.0 | 22.6 | 22.6 |
| Product (Kg/hr) | 990.4 | 21.3 | 969.1 | 16.2 | 952.1 | 0.4 | 16.6 | 16.6 |
| Solvent (Kg/hr) | 998.0 | 10.4 | 987.6 | 0.3 | 987.3 | 987.3 | 987.6 | 987.6 |
| Heavy (kg/hr) | 50.7 | 0.0 | 50.7 | 0.0 | 50.7 | 3.2 | 3.2 | 3.2 |

\* Lights: Substance having molecular weight lower than that of hexane in ethylene impurities and by-products
\* Heavy: Substance having molecular weight higher than that of octane in by-products
\* Product: mixture of hexene and octene
\* Steam 1: second discharge stream of reactor 100 fed from reactor 100 to second separation device 210
\* Stream 2: Upper discharge stream of second separation device 210
\* Stream 3: Lower discharge stream of second separation device 210
\* Stream 4: Upper discharge stream of third separation device 220
\* Stream 5: Lower discharge stream of third separation device 220
\* Stream 6: Solvent stream fed to monomer dissolution device 300
\* Stream 7: Discharge stream of monomer dissolution device 300
\* Stream 8: Stream fed from pump 400 to reactor 100

Referring to Table 1, it can be confirmed that a temperature of the stream 2 is 40° C. and a temperature of the stream 4 is 54° C., which are low temperatures. Thus, condensers (not illustrated) installed above the second separation device and the third separation device may condense upper discharge streams of the second and third separation devices using a coolant without using a separate refrigerant. Thus, energy can be saved compared to a process using the refrigerant.

In addition, it can be confirmed that in the stream 7, ethylene recovered as the stream 4 is dissolved at a dissolution rate of 100%. In this case, it can be confirmed that in the stream 7, a temperature at which the recovered ethylene is dissolved in a solvent in the monomer dissolution device 300 and is then discharged is 41° C., which is a significantly higher temperature than a cooling temperature of the recovered ethylene of −25° C. or less in the related art.

In addition, it can be confirmed that a temperature of the stream 3 is 200° C. or less, such that a reaction of hydrocarbons at a high temperature is suppressed to prevent loss of an oligomer product.

Comparative Example

Figure 2:
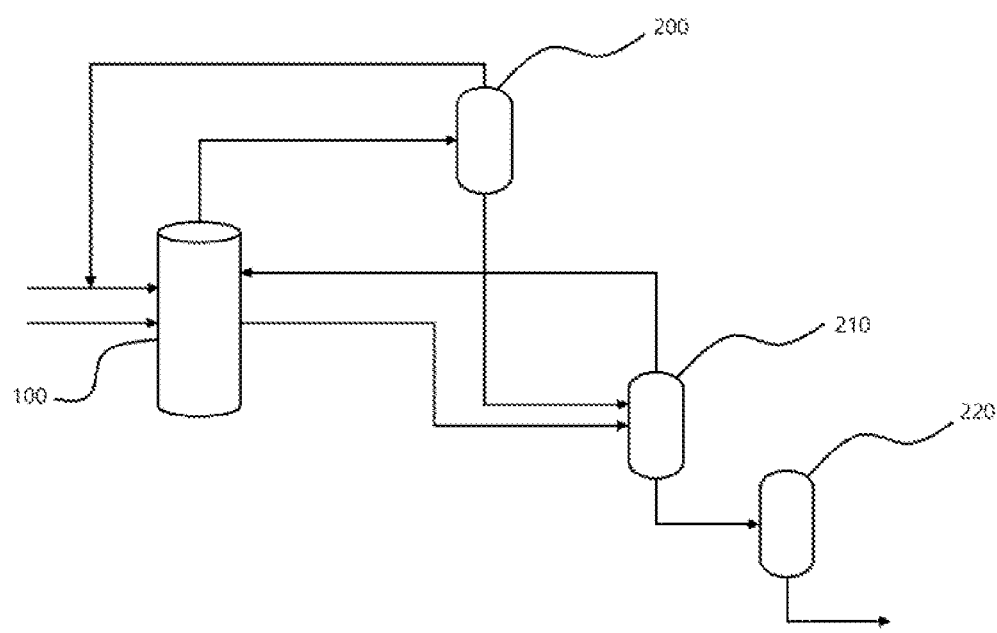
FIG. 2 is a process flowchart of a method for preparing an oligomer according to comparative examples.

For the process flowchart illustrated in FIG. 2, a process was simulated using Aspen Plus simulator commercially available from Aspen Technology, Inc. In this case, ethylene (C2) as a monomer was fed to the reactor 100 at 1,000 kg/hr, reaction conditions of the reactor 100 were set so that a temperature was 70° C. and a pressure was 30 bar, methylcyclohexane was used as the solvent, and an amount of fed solvent fed to the reactor 100 was 1 time the sum of a product and a by-product in a second discharge stream fed from the reactor 100 to the second separation device 210. The results are shown in Table 2 below.

TABLE 2

|  | Stream 1-1 | Stream 2-1 | Stream 3-1 | Stream 5-1 | Stream 6-1 |
|---|---|---|---|---|---|
| Phase | Liquid-phase | Gas-phase | Liquid-phase | Gas-phase | Liquid-phase |
| Temperature (° C.) | 70 | 0 | 263 | 161 | 34 |
| Pressure (bar) | 30 | 30 | 30 | 6 | 30 |
| Total flow rate (Kg/hr) | 2355.1 | 352.7 | 2002.4 | 1990.1 | 990.8 |
| Lights (kg/hr) | 37.5 | 30.0 | 7.5 | 0.1 | 0.0 |
| Ethylene (Kg/hr) | 323.2 | 321.9 | 1.3 | 0.0 | 0.0 |
| Product (Kg/hr) | 954.9 | 0.8 | 954.1 | 952.1 | 0.4 |
| Solvent (Kg/hr) | 988.7 | 0.0 | 988.7 | 987.3 | 987.3 |
| Heavy (kg/hr) | 50.8 | 0.0 | 50.8 | 50.7 | 3.2 |

\* Lights: Substance having molecular weight lower than that of hexane in ethylene impurities and by-products
\* Heavy: Substance having molecular weight higher than that of octane in by-products
\* Product: Mixture of hexene and octene
\* Steam 1-1: Second discharge stream of the reactor 100 fed from reactor 100 to second separation device 210
\* Stream 2-1: Upper discharge stream of second separation device 210
\* Stream 3-1: Lower discharge stream of second separation device 210
\* Stream 5-1: Lower discharge stream of third separation device 220
\* Stream 6-1: Solvent stream fed to reactor 100

Referring to Table 2, a temperature of the stream 2-1 is 0° C., and a condenser (not illustrated) installed above the second separation device necessarily require a refrigerant in order to condense the upper discharge stream of the second separation device.

In addition, a temperature of the stream 3-1 is 250° C. or more, such that it is difficult to use a steam as a heat source of a reboiler (not illustrated) installed under the second separation device, and hot oil should thus be used.

This causes an increase in a process cost and an energy cost, and causes production of by-products and loss of a raw material due to a reaction of hydrocarbons at a high temperature.

The invention claimed is:

1. A method for preparing an oligomer, the method comprising:
    performing an oligomerization reaction by feeding a feed stream containing a monomer to a reactor;
    feeding a first discharge stream of the reactor to a first separation device and feeding a second discharge stream of the reactor to a second separation device;
    feeding a lower discharge stream of the second separation device to a third separation device;
    feeding an upper discharge stream containing the monomer of the third separation device to a monomer dissolution device and dissolving the upper discharge stream in a solvent fed to the monomer dissolution device; and
    feeding a discharge stream of the monomer dissolution device to the reactor,
    wherein the discharge stream of the monomer dissolution device is a liquid-phase stream containing the monomer dissolved in the solvent.

2. The method of claim 1, wherein the second separation device is operated at a higher pressure than the third separation device.

3. The method of claim 2, wherein a pressure in the second separation device is 10 bar to 50 bar, and a pressure in the third separation device is 0.5 bar to 15 bar.

4. The method of claim 1, wherein the lower discharge stream of the second separation device contains the monomer.

5. The method of claim 1, wherein a pressure of the upper discharge stream of the third separation device is 0.5 bar to 15 bar.

6. The method of claim 1, wherein the upper discharge stream of the third separation device is a gas-phase stream.

7. The method of claim 1, wherein a temperature of the discharge stream of the monomer dissolution device is in a range of −5° C. to 50° C.

8. The method of claim 1, wherein a pressure of the discharge stream of the monomer dissolution device is 1 bar to 100 bar.

9. The method of claim 1, wherein the method satisfies General Equation 1:

$$M2/M1 \times 100 \geq 90\% \qquad \text{[General Equation 1]}$$

wherein M1 is a monomer content in the upper discharge stream of the third separation device, and M2 is a monomer content in the discharge stream of the monomer dissolution device.

10. The method of claim 1, wherein the solvent is at least one selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

11. The method of claim 1, wherein the monomer is ethylene and the oligomer is alpha-olefin.

12. An apparatus for preparing an oligomer, the device comprising:
    a reactor oligomerizing a feed stream containing a monomer, feeding a first discharge stream to a first separation device, and feeding a second discharge stream to a second separation device;
    the first separation device receiving the first discharge stream of the reactor;
    the second separation device receiving the second discharge stream of the reactor and feeding a lower discharge stream to a third separation device;
    the third separation device receiving the lower discharge stream of the second separation device and feeding an upper discharge stream containing the monomer to a monomer dissolution device; and
    the monomer dissolution device dissolving the fed upper discharge stream of the third separation device in a separately fed solvent and feeding a discharge stream to the reactor,
    wherein the discharge stream of the monomer dissolution device is a liquid-phase stream containing the monomer dissolved in the separately fed solvent.

* * * * *